(12) United States Patent
Andrasi et al.

(10) Patent No.: US 6,602,865 B1
(45) Date of Patent: Aug. 5, 2003

(54) PYRIDAZINO(4,5-B)(1,5)OXAZEPINONE, -THIAZEPINONE AND -DIAZEPINONE COMPOUNDS

(75) Inventors: Ferenc Andrasi, Budapest (HU); Agnes Angyal nee Pataky, Budapest (HU); Pal Berzsenyi, Budapest (HU); Sandor Boros, Szod (HU); Laszlo Harsing, Budapest (HU); Katalin Horvath, Budapest (HU); Peter Matyus, Budapest (HU); Imre Moravcsik, Budapest (HU); Agnes Papp nee Behr, Budapest (HU); Antal Simay, Budapest (HU); Erzsebet Szabo nee Bagdy, Budapest (HU); Katalin Szabo nee Pusztai, Budapest (HU); Istvan Tarnawa, Budapest (HU); Ildiko Varga, Budapest (HU)

(73) Assignee: IVAX Drug Research Institute, Ltd., Budapest (HU)

( * ) Notice: Subject to any disclaimer, the term of this patent is extended or adjusted under 35 U.S.C. 154(b) by 0 days.

(21) Appl. No.: 09/439,847

(22) Filed: Nov. 15, 1999

Related U.S. Application Data

(60) Provisional application No. 60/108,513, filed on Nov. 16, 1998.

(51) Int. Cl.⁷ .................. A61K 31/55; A61P 25/00; C07D 487/02; C07D 513/02
(52) U.S. Cl. .................. 514/211.06; 514/211.07; 514/211.09; 514/221; 540/491; 540/502; 540/552; 540/568
(58) Field of Search .................. 514/211.06, 211.07, 514/211.09, 221; 540/491, 552, 568, 502

(56) References Cited

U.S. PATENT DOCUMENTS 5,753,664 A * 5/1998 Aono et al. .................. 514/258

OTHER PUBLICATIONS

Mátyus et al., *Bioorganic and Medicinal Chemistry Letters*, vol. 7, No. 22, pp. 2857–2862, 1997.

* cited by examiner

Primary Examiner—Brenda Coleman

(57) ABSTRACT

Pyridazino(4,5-b)(1,5)oxazepinone, thiazepinone and diazepinone compounds of formula(I)

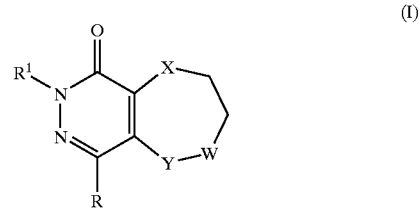

and their tautomers and the acid-addition salts of all these compounds show memory-enhancing and neuroprotective properties.

7 Claims, No Drawings

PYRIDAZINO(4,5-B)(1,5)OXAZEPINONE, -THIAZEPINONE AND -DIAZEPINONE COMPOUNDS

This application claims the benefit of U.S. Provisional Application No. 60/108,513, filed Nov. 16, 1998. The invention relates to pyridazino(4,5-b)(1,5)oxazepinone, -thiazepinone and -diazepinone compounds, as well as to pharmaceutical compositions containing these compounds.

The invention relates to novel pyridazino[4,5-b][1,5] oxazepinone, -thiazepinone and -diazepinone derivatives as well as to pharmaceutical compositions containing these compounds.

The compounds according to the invention have valuable biological properties, namely, they show significant memory-enhancing effect, which is associated with considerable neuroprotective character.

DESCRIPTION OF THE PRIOR ART

According to a nowadays accepted view, glutamate the most important neurotransmitter of stimulating character, plays a decisive role in the memory processes. In pathological conditions resulting in dementia, the underfunction of the glutamatergic system can be demonstrated [Danysz W. et al., Drug News & Persp., 8, 263 (1995)]. The role of ionotropic glutamate receptors of the NMDA type played in memory functions has been experimentally proved; following their special, voltage-dependent activation the calcium permeability is enhanced, whereby certain memory processes can be readily explained on the neuronal level. Accordingly, compounds having glutamate agonist effect may stimulate the cognitive functions [Granger, R. et al., Synapse, 15, 326 (1993); Nicholson, C. D. et al., Psychopharmacology, 101, 147 (1994)). The effect of aniracetame and related compounds, which are long used in the therapy as memory-enhancers, is also based on the potentiation of the glutamate neurotransmission [Ito, l. et al., J. Physiol., 424, 533 (1990)].

Overactivity of the glutamatergic system, however, can result in excitotoxicity-induced neuronal cell loss, which is observed in several neurodegenerative disorders. In such diseases glutamate agonists can counter-balance the memory deficit resulted from the neuronal damage, while neuroprotective effect can be expected from glutamate antagonists.

Now it has been found that the novel compounds according to the invention are very effective in in vivo memory models, wherein they simultaneously show NMDA-activating and AMPA-inhibiting effects. Such novel type drugs of combined effect may result in definite advantages over the known memory-enhancing agents. Namely, reduced risk of side-effects (e.g. epileptogenic or neurone-damaging effect) inherently associated with the target effects (i.e. enhancing glutamatergic neurotransmission) during long-term use can be expected. Further, the AMPA antagonist character of the compounds can result in moderation of excitotoxicity-related neurodegeneration. Thus, besides palliative treatment the compounds of the invention may also slow down the progress of the diseases.

Some derivates of formula (I) of the present invention, in which R stands for hydrogen atom, $R^1$ is methyl group, X is oxygen or sulphur atom, W is methylene group and Y stands for a group of formula $NR^3$, wherein $R^3$ is hydrogen atom or benzyl group, are mentioned in the literature as intermediates in the synthesis of novel pyridazino [4,5-b][1,5] oxazepines [P. Matyus et al.: Bioorganic and Medicinal Chemistry Letters, Vol. 7, No. 22, pp. 2857–2862 (1997)], but the synthesis, the physical data and the biological activity of these compounds has not been described so far.

DESCRIPTION OF THE INVENTION

The invention relates to novel pyridazino[4,5-b][1,5] oxazepinone, -thiazepinone and -diazepinone derivatives of general formula (I)

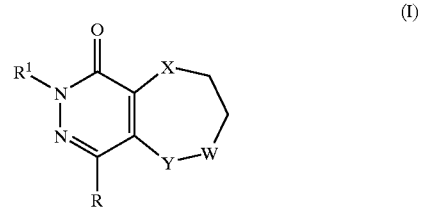

wherein
R stands for hydrogen atom or a group of formula $NHR^4$, wherein $R^4$ stands for hydrogen, $C_{1-4}$ alkyl or $C_{2-5}$ acyl group,
$R^1$ stands for $C_{1-4}$ alkyl or $C_{2-4}$ alkenyl group, which may be substituted by a phenyl group, or phenyl group,
W stands for methylene or carbonyl group,
X and Y stand independently for oxygen or sulphur atom, SO, $SO_2$ or $NR^3$ group, wherein $R^3$ is hydrogen atom, $C_{1-4}$ alkyl group or a group of formula (II),

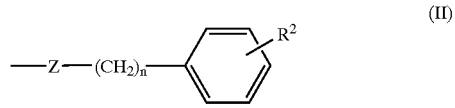

wherein $R^2$ stands for hydrogen or halogen atom, $C_{1-4}$ alkoxy or nitro group or a group of formula $NHR^4$, wherein $R^4$ has the above meaning, and Z stands for methylene or carbonyl group, further n has a value of 0, 1 or 2,
with the proviso that when any of X or Y stands for oxygen or sulphur atom, SO or $SO_2$ group or a group of formula $NR^3$,
wherein $R^3$ stands for hydrogenatom or a $C_{1-4}$ alkyl group, then the other may stand only for an $NR^3$ group, wherein $R^3$ stands for a group of formula (II)—wherein $R^2$, Z and n have the above meaning
and their tautomers and the acid-addition salts of all these compounds. Furthermore, the invention relates to pharmaceutical compositions containing the compounds of general formula (I) as active agents.

In the general formula (I) the alkyl, acyl and alkenyl groups may have straight or branched chain, and the term "halogen atom" relates to chlorine or bromine atom.

The salts of the compounds of general formula (I) are pharmaceutically acceptable salts formed with inorganic and organic acids. Inorganic acids suitable for this purpose are e.g. hydrochloric acid, hydrobromic acid, phosphoric acid and sulphuric acid. From the organic acids to be used for this purpose acetic acid, acetic acid, maleic and fumaric acid, succinic acid, lactic acid, tartaric acid, citric acid and methanesulphonic acid are mentioned.

A preferred group of the compounds according to the invention of general formula (I) comprises compounds wherein R is hydrogen atom, $R^1$ stands for methyl or cinnamyl group, X is oxygen or sulphur atom or a group of formula $NCH_3$, W is methylene group and Y stands for a group of formula NR³, wherein R³ is a benzyl or a substituted benzyl group. Especially preferred are those compounds wherein X stands for sulphur atom.

The compounds of general formula (I) according to the invention can be prepared e.g. by the intramolecular cyclization of a compound of general formula (IIIa)

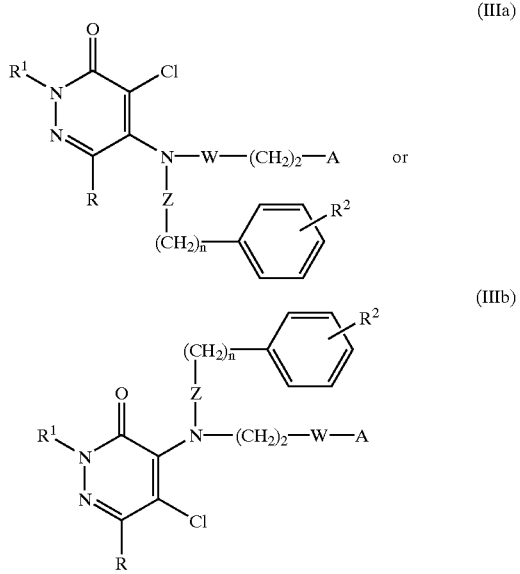

wherein A is a hydroxyl group or a halogen atom—and, if desired, by the subsequent transformation of the substituents.

a) For preparing compounds of general formula (I), wherein one of X and Y stands for a group of formula NR³—wherein R³ is a group of general formula (II), wherein R², Z and n have the above meanings—and the other stands for oxygen atom, a compound of general formula (IIIa) or (IIIb)—wherein A stands for hydroxyl group, and R, R¹, R², W, Z and n have the above meaning— is reacted with a base, e.g. sodium ethylate.

b) For preparing compounds of general formula (I), wherein one of X and Y stands for a group of formula NR³—wherein R³ is a group of general formula (II), wherein R², Z and n have the above meaning—and the other stands for sulphur atom, a compound of general formula (IIIa) or (IIIb), wherein A stands for halogen atom, and R, R¹, R², W, Z and n have the above meaning, is reacted with an inorganic sulphide, e.g. sodium sulphide.

c) For preparing compounds of general formula (I), wherein one of X and Y stands for a group of formula NR³—wherein R³ stands for a group of general formula (II), wherein R², Z and a have the above meaning—and the other stands for a group of formula NR³, wherein R³ is hydrogen atom or a $C_{1-4}$ alkyl group—a compound of general formula (IIIa) or (IIIb), wherein A is halogen atom, and R, R¹, R², W, and n have the above meaning, is reacted with ammonia or an aliphatic amine.

d) For preparing compounds of general formula (I)—wherein one of X and Y stands for a group of formula NR³, wherein R³ is a group of general formula (II)—wherein R², Z and n have the above meaning—and the other is an SO or SO₂ group, a compound of general formula (I)—wherein one of X and Y is a group of formula NR³, wherein R³ stands for a group of formula (II), wherein R², Z and n have the above meaning—and the other is a sulphur atom, is reacted with an oxidating agent (e.g. alkali metaperiodate or hydrogen peroxide).

e) For preparing compounds of general formula (I)—wherein one of X or Y is a group of formula NR³, wherein R³ has a meaning different from benzyl group—a compound of general formula (I), wherein R, R¹ and W has the above meaning, further one of X and Y stands for a group of formula NR³ —wherein R³ is a benzyl group—and the other is oxygen or sulphur atom or a SO, SO₂ or NR³ group, wherein R³ is hydrogen atom or a $C_{1-4}$ alkyl group—is debenzylated in a known way, whereafter the product is reacted with an acid halide or alkyl halide corresponding to the desired group of general formula (II).

As mentioned above, the compounds of general formula (I) according to the invention have valuable biological activity, namely, they possess considerable memory-enhancing effect accompanied by valuable neuroprotective character.

The memory-enhancing effect of the compounds according to the invention was measured by counter-balancing the scopolamine-induced memory-deficit in rats, with oral doses of 50 mg/kg, in the passive avoidance test published by Cumin, R. et al. [Psychopharmacology, 78, 104 (1982)].

The results obtained are summarized as follows:

| No. of Example | Memory improvement compared to amnesic control (%) |
|---|---|
| 3 | 100 |
| 4 | 100 |
| 7 | 250 |
| 11 | 328 |

The AMPA antagonistic effect of the compounds was tested on rat Purkinje cells (Bleakman, D. et al., Neuropharmacology, 35, 1689 (1996)] in a concentration of 100 µM, in a patch clamp experiment [Yamada, K. A. and Turetsky, D. M., Br. J. Pharmacol., 117, 1663 (1996)].

| No. of Example | AMPA antagonistic effect in patch clamp test (inhibition of ion current in %) |
|---|---|
| 4 | 30.05 |
| 5 | 24.15 |
| 11 | 64.46 |
| 12 | 37.27 |
| 15 | 30.97 |

The AMPA antagonistic effect of the compounds was also tested on spreading depression of chick retina (Sheardown, M. J.: Brain Res., 1993, 607, 189) in a concentration of 20 µM.

| No. of Example | Antagonistic effect on AMPA-induced spreading depression (%) |
|---|---|
| 3 | 10 |
| 4 | 17 |
| 7 | 16 |
| 11 | 28 |
| 12 | 32 |
| 13 | 48 |

The NMDA receptor-mediated inward current evoked by the compounds was tested on rat hippocampal cell culture (Baughman, R. W. et al. in: Culturing Nerve Cells, 1992, pp. 227) in a concentration of 100 µM in a patch clamp experiment.

| No. of Example | Inward current evoked by the test compound (%) |
|---|---|
| 11 | 100 |
| 12 | 244 |
| 13 | 178 |

It is expected that the compounds of general formula (I) according to the invention can be advantageously used for the manufacture of medicaments suitable for treating acute or chronic neurodegenerative diseases and/or different memory disorders, especially when the memory loss is associated with neurodegeneration of excitotoxic origin such as e.g. Alzheimer's disease, Huntington's chorea, Parkinson's disease, further dementias of AIDS origin or of vascular origin in aged people For therapeutic purposes the compounds according to the invention of general formula (I) are transformed to enteral or parenteral pharmaceutical preparations. For this purpose organic or inorganic carriers and fillers generally used in the pharmaceutical industry can be employed, such as water, gelatine, arabic gum, lactose, starch, magnesium stearate, talc, plant oils, polyethylene glycols etc. The pharmaceutical composition may be of solid form such as tablets, dragees, suppositories or capsules, or it can be prepared in liquid form such as solutions, suspensions or emulsions. The above-mentioned auxiliaries can be supplemented with preserving, stabilizing, emulsifying, buffering etc. additive agents, too.

For parenteral administration the active agent is formulated as a sterile solution or suspension; in such cases the sterile carrier may contain as an adjuvant e.g. a local anesthetic, a stabilizing and/or a buffering agent.

The dose to be administered to the patient depends on several factors such as the method of use, the type and severity of the disease as well as the weight and age of the patient. The daily dose may amount to 0.5–1000 mg, preferably 20–200 mg and can be administered at once or divided to several parts.

The invention also relates to a method of treating conditions associated with the acute or chronic form of neurodegenerative diseases and/or different memory disorders, especially when the memory loss is associated with neurodegeneration of excitotoxic origin such as e.g. Alzheimer's disease, Huntington's chorea and Parkinson's disease, and more specifically, a method of treating mammals, which comprises the administration of the compounds of general formula (I) as the active agent.

The compounds according to the invention and the processes for their preparation are illustrated by the following non-limiting Examples.

EXAMPLE 1

8-Methyl-5-(4-nitrobenzoyl)-2,3,4,5-tetrahydro-9(8H)-pyridazino[4,5-b][1,5]thiazepinone To a suspension of 0.8 g (4.06 mmol) of 8-methyl-2,3,4,5-tetrahydro-9(8H)-pyridazino[4,5-b][1,5]thiazepinone in 8 ml of anhydrous pyridine 0.99 g (5.33 mmol) of 4-nitrobenzoyl chloride is added, whereafter the suspension is stirred for 18–20 hours at 55–60° C., while adding every 4 hours 0.5 g (2.54 mmol) of 4-nitrobenzoyl chloride. The reaction mixture is poured on 60 ml of icy water and extracted with 3×50 ml of dichloromethane. The organic phase is washed with 2×50 ml of 2 M hydrochloric acid solution, then with 30 ml of saturated sodium hydrogen carbonate solution and 2×60 ml of water. The organic phase is dried, filtered and evaporated. The residue is purified by column chromatography. In this way 1.08 g (77%) of the title compound is obtained with a melting point of 230–232° C.

EXAMPLE 2

5-(2-Phenylacetyl)-8-methyl-2,3,4,5-tetrahydro-9(8H)-pyridazino[4,5-b][1,5]thiazepinone The title compound is prepared by the method of Example 1, with the difference that the acylation is carried out with phenyl-acetyl chloride, instead of with 4-nitrobenzoyl chloride.

Yield: 50%, mp.: 133° C.

EXAMPLE 3

5-Benzoyl-8-methyl-2,3,4,5-tetrahydro-9(8H)-pyridazino[4,5-b][1,5]thiazepinone

The title compound is prepared by the method of Example 1, with the difference that the acylation is carried out with benzoyl chloride, instead of with 4-nitro-benzoyl-chloride.

Yield: 51%, mp.: 210° C.

EXAMPLE 4

5-Benzyl-8-methyl-2,3,4,5-tetrahydro-9(8H)-pyridazino[4,5-b][1,5]oxazepinone 3.45 g (150 mmol) of sodium metal are dissolved in 150 ml of anhydrous ethanol, then 15.40 g (50 mmol) of 5-[N-benzyl-N-(3-hydroxy-propil)-amino]-4-chloro-2-methyl-3(2H)-pyridazinone are added. The reaction mixture is boiled for 6 hours, then it is evaporated. 80 ml of water are added to the evaporation residue, then it is extracted with 3×100 ml of ethyl acetate. The organic phase is dried, filtered and evaporated. The residue is triturated with 20 ml of ethyl acetate, filtered, washed and dried. In this way 9.95 g (73%) of the title compound are obtained with a melting point of 113–115° C.

EXAMPLE 5

5-(4-Methoxybenzyl)-8-methyl-2,3,4,5-tetrahydro-9(8H)-pyridazino[4,5-b][1,5]oxazepinone The title compound is prepared by the method of Example 4, starting from 5-[N-(4-methoxybenzyl)-N-(3-hydroxypropyl)amino]-2-methyl-4-chloro-3(2H)-pyridazinone.

Yield: 36%, mp.: 92–93° C.

EXAMPLE 6

5-Benzyl-8-benzyl-2,3,4,5-tetrahydro-9(8H)-pyridazino[4,5-b][1,5]oxazepinone

The title compound is prepared by the method of Example 4, starting from 5-[N-benzyl-N-(3-hydroxypropyl)amino]-4-chloro-2-benzyl-3(2H)-pyridazinone.

Yield: 42%, mp.: 70° C.

EXAMPLE 7

5-Benzyl-8-cynnamyl-2,3,4,5-tetrahydro-9(8H)-pyridazino[4,5-b][1,5]oxazepinone

The title compound is prepared by the method of Example 4, starting from 5-[N-benzyl-N-(3-hydroxypropyl)amino]-4-chloro-2-cinnamyl-3(2H)-pyridazinone.

Yield: 56%, oil.

EXAMPLE 8

6-Amino-5-benzyl-8-methyl-2,3,4,5-tetrahydro-9 (8H)-pyridazino[4,5-b][1,5]oxazepinone The title compound is prepared by the method of Example 4, starting from 6-amino-5-[N-benzyl-N-(3-hydroxypropyl) amino]-4-chloro-2-methyl-3(2H)-pyridazinone.

Yield: 56%, mp.: 195–196° C.

EXAMPLE 9

5-Benzyl-7-methyl-2,3,4,5-tetrahydro-6(7H)-pyridazino[4,5-b][1,5]oxazepinone

The title compound is prepared by the method of Example 4, starting from 4-[N-benzyl-N-(3-hydroxypropyl)amino]-5-chloro-2-methyl-3(2H)-pyridazinone.

Yield: 86%, mp, 82–86° C.

EXAMPLE 10

5-Benzyl-7-cinnamyl-2,3,4,5-tetrahydro-6(7H)-pyridazino[4,5-b)[1,5]oxazepinone

The title compound is prepared by the method of Example 4, starting from 4-[N-benzy]-N-(3-hydroxypropyl)amino]-5-chloro-2-cinnamyl-3(2H)-pyridazinone.

Yield: 85%, mp.; oil.

EXAMPLE 11

5-Benzyl-8-methyl-2,3,4,5-tetrahydro-9(8H)-pyridazino[4,5-b][1,5]thiazepinone

To a solution of 7.0 g (21 mmol) of 5-[N-benzyl-N-(3-chloropropyl)-amino]-4-chloro-2-methyl-3(2H)-pyridazinone in 70 ml of methanol a solution of 12.8 g (53 mmol) of sodium sulphide nonahydrate in 7 ml of water is added at room temperature, while stirring. The mixture is boiled for 2 hours while stirring, then it is cooled to room temperature, filtered and the methanol is evaporated in vacuum from the filtrate. 50 ml of water are added to the aqueous residue and the mixture is extracted with 3×50 ml of ethyl acetate. The organic phase is dried and evaporated in vacuum. The residue is triturated with a small portion of cold ethyl acetate, then it is filtered and washed with cold diethyl ether. In this way 3.57 g (58%) of the title compound are obtained with a melting point of 108–109° C.

EXAMPLE 12

5-(4-Chlorobenzyl)-8-methyl-2,3,4,5-tetrahydro-9 (8H)-pyridazino[4,5-b]-[1,5]thiazepinone The title compound is prepared by the method of Example 11 from 5-[N-(4-chlorobenzyl)-N-(3-chloropropyl)amino]-4-chloro-2-methyl-3(2H)-pyridazinone.

Yield: 28%, mp.: 106–109° C.

EXAMPLE 13

5-Benzyl-8-phenyl-2,3,4,5-tetrahydro-9(8H)-pyridazino[4,5-b]-[1,5]thiazepinone

The title compound is prepared by the method of Example 11 from 5-[N-benzyl-N-(3-chloropropyl)amino]-4-chloro-2-phenyl-3(2H)-pyridazinone.

Yield: 54%, mp.: 174–175° C.

EXAMPLE 14

5-Benzyl-7-methyl-2,3,4,5-tetrahydro-6(7H)-pyridazino[4,5-b][1,5]thiazepinone

The title compound is prepared by the method of Example 11 from 4-[N-benzyl-N-(3-chloropropyl)amino]-5-chloro-2-methyl-3(2H)-pyridazinone.

Yield: 22%, mp.: 112–114° C.

EXAMPLE 15

1-Benzyl-5,7-dimethyl-2,3,4,5-tetrahydro-6(7H)-pyridazino[4,5-b][1,5]diazepinone 0.65 g (2 mmol) of 5-[N-benzyl-N-(3-chloropropyl) amino]-4-chloro-3-methyl-3(2H)-pyridazinone are weighed into an autoclave. 5 ml of 33% methylamine solution in ethanol are added. The mixture is warmed for 100 minutes at an inner temperature of 120° C., then it is evaporated. The residue is taken up in 10 ml of dichloromethane and shaken with 2×5 ml of water. The dichloromethane phase is dried over sodium sulphate and then evaporated. The residue is purified by column chromatography (adsorbent: silicagel, eluent:9:1 mixture of ethyl-acetate and methanol).

Yield: 0.25 g (45%), mp.: 87–89° C.

EXAMPLE 16

5-Benzyl-8-cinnamyl-2,3,4,5-tetrahydro-9(8H)-pyridazino[4,5-b][1,5]thiazepinone

To a solution of 4.0 g (9.34 mmol) of 5-[N-benzyl-N-(3-chloro-propyl)-amino]-4-chloro-2-cinnamyl-3(2H)-pyridazinone in 40 ml of dimethyl sulphoxide 4.4 g (18 mmol) of sodium-sulphide nonahydrate are added at room temperature while stirring. The mixture is stirred at room temperature for 2 hours, then it is poured to 150 ml of water and extracted with 3×100 ml of ethyl acetate. The organic phase is dried and evaporated in vacuum. The residue is purified by column chromatography. In this way 0.75 g (20%) of the title compound is obtained with a melting point of 101–102° C.

EXAMPLE 17

5-Benzyl-8-methyl-4-oxo-2,3,4,5-tetrahydro-9(8H)-pyridazino[4,5-b][1,5]thiazepinone The title compound is prepared by the method of Example 16 from 5-[N-benzyl-N-(3-chloropropionyl)amino]-4-chloro-2-methyl-3(2H)-pyridazinone.

Yield: 27%, mp.: 154–155° C.

EXAMPLE 18

5-Benzyl-8-methyl-2,3,4,5-tetra hydro-9(8H)-pyridazino[4,5-b][1,5]thiazepinone-1-oxide To a solution of 0.84 g (2.92 mmol) of 5-benzyl-8-methyl-2,3,4,5-tetrahydro-9(8H)-pyridazino[4,5-b][1,5] thiazepinone in 7.5 ml of glacial acetic acid the solution of 0.75 g (3.6 mmol) of sodium metaperiodate in 6 ml of water are added dropwise while stirring and cooling with ice-water. The reaction mixture is stirred for 3 hours while cooling with ice-water. The obtained suspension is filtered and washed with a small amount of water. The aqueous phase is extracted with 3×20 ml of dichloromethane. The organic phase is washed with 2×5 ml of 10% aqueous sodium carbonate solution and then with 2×10 ml of water. The organic phase is dried and evaporated in vacuum. The residue is crystallized from a 9:1 mixture of ethyl acetate and methanol. In this way 0.56 g (63%) of the title compound is obtained with a melting point of 162–163° C.

EXAMPLE 19

5-Benzyl-8-methyl-2,3,4,5-tetrahydro-9(8H)-pyridazino[4,5-b][1,5]thiazepinone-1,1-dioxide A mixture of 0.60 g (1.98 mmol) of 5-benzyl-8-methyl-2,3,4,5-tetrahydro-9(8H)-pyridazino[4,5-b][1,5]

thiazepinone-1-oxide, 1.92 ml of glacial acetic acid and 1.2 ml of 30% aqueous hydrogen peroxide are left to stand for a day. The precipitated crystals are filtered, washed acid free with water and dried in an exsiccator. In this way 0.35 g (55%) of the title compound are obtained with a melting point of 288–290° C.

Preparation of the starting compounds used in the Examples

EXAMPLE 20

5-[N-Benzyl-N-(3-hydroxypropyl)amino]-4-chloro-2-methyl-3(2H)-pyridazinone

A solution of 11.48 g (64,1 mmol) of 4,5-dichloro-2-methyl-3(2H)-pyridazinone and 31.84 g (193.0 mmol) of 3-(N-benzylamino)propanol in 250 ml of water is boiled for 25 hours while stirring. The mixture is cooled, its pH is set with concentrated hydrochloric acid to 3 and it is extracted with 2×400 ml of ethyl acetate. The organic phase is dried and evaporated, 10 ml of ethyl acetate are added to the evaporation residue, then it is left to stand overnight at −10° C. The precipitated crystals are filtered and washed with ethyl acetate and then with diethyl ether. In this way 10.60 g (54%) of the title compound are obtained with a melting point of 94–95° C.

EXAMPLE 21

4-[N-Benzyl-N-(3-hydroxypropyl)amino]-5-chloro-2-methyl-3(2H)-pyridazinone

When the ethyl acetate mother liquor of the above reaction is evaporated and purified by column chromatography, 2.96 g (15%) of the title compound are obtained in the form of an oil.

The compounds according to the following Examples 22–15 are prepared by the method of Example 20.

EXAMPLE 22

5-[N-(4-Methoxybenzyl)-N-(3-hydroxypropyl)amino]-2-methyl-4-chloro-3(2H)-pyridazinone Yield: 28%, oil.

EXAMPLE 23

5-[N-Benzyl-N-(3-hydroxypropyl)amino]-4-chloro-2-methyl-6-nitro-3(2H)-pyridazinone Yield: 47%, mp.: 94° C.

EXAMPLE 24

5-[N-Benzyl-N-(3-hydroxypropyl)amino]-4-chloro-2-benzyl-3(2H)-pyridazinone

Yield: 52%, mp.: 95–96° C.

EXAMPLE 25

5-[N-Benzyl-N-(3-hydroxypropyl)amino]-4-chloro-2-cinnamyl-3(2H)-pyridazinone

Yield: 43%, oil.

EXAMPLE 26

6-Amino-5-[N-benzyl-N-(3-hydroxypropyl)amino]-4-chloro-2-methyl-3(2H)-pyridazinone 16.40 g (46.5 mmol) of 5-[N-benzyl-N-(3-hydroxypropyl)amino]-4-chloro-2-methyl-6-nitro-3(2H)-pyridazinone (see above) are dissolved in 300 ml of glacial acetic acid. 25.3 g (453.0 mmol) of iron powder are added to the solution while stirring and cooling in such a rate that the temperature of the reaction mixture remains below 25° C. The stirring is continued for further 8 hours at room temperature. Then the unreacted iron powder and the iron (II)salts formed during the reaction are filtered off and the filtrate is evaporated. The evaporation residue is boiled in 2×300 ml of ethyl acetate and then decanted. The ethyl acetate solution is washed with 2×15 ml of water, dried and evaporated. In this way 8.71 g (61) %) of the title product arc obtained with a melting point of 111–113° C.

EXAMPLE 27

5-[N-Benzyl-N-(3-chloro propyl)amino]-4-chloro-2-methyl-3(2H)-pyridazinone

To a solution of 10.00 g (32 mmol) of 5-[N-benzyl-N-(3-hydroxypropyl)amino]-4-chloro-2-methyl-3(2H)-pyridazinone in 100 ml of dichloromethane 3.5 ml (5.5 g, 46 mmol) of thionyl chloride are added dropwise while stirring. If necessary, a catalytic amount of 4-(N,N-dimethyl amino) pyridine is added to the solution. The reaction mixture is boiled for 14 hours, then cooled and evaporated. The evaporation residue is triturated with diethyl ether. The crystals are filtered off and washed with diethyl ether. In this way 9.50 g (95%) of the title compound are obtained with a melting point of 92–93° C.

The compound of Example 28 is prepared by the method of Example 27.

EXAMPLE 28

4-[N-Benzyl-N-(3-chloropropyl)amino]-5-chloro-2-methyl-3(2H)-pyridazinone

Yield: 98%, oil.

EXAMPLE 29

8-Methyl-2,3,4,5-tetrahydro-9(8H)-pyridazino[4,5-b][1,5]oxazepinone 13.00 g (48.0 mmol) of 5-benzyl-8-methyl-2,3,4,5-tetrahydro-9(8H)-[4,5-b][1,5]oxazepinone are boiled in 100 ml of ethanol with 7.3 ml of freshly distilled cyclohexene and 1.56 g of 10% palladium on charcoal catalyst for 1 hour while stirring. Then the catalyst is filtered off from the reaction mixture and washed with 2×20 ml of ethanol. The filtrate is evaporated to a volume of 30 ml and then it is left to stand in a refrigerator overnight. The precipitated crystals are filtered and washed with cold ethanol. In this way 6.80 g (78%) of the title compound are obtained. After evaporating the mother liquor the residue is recrystallized from ethanol, whereby further 1.10 g (12%) of the title compound are obtained with a melting point of 180–182° C.

EXAMPLE 30

8-Methyl-2,3,4,5-tetrahydro-9(8H)-pyridazino[4,5-b][1,5]thiazepinone

To a solution of 13.10 g (45.5 mmol) 5-benzyl-8-methyl-2,3,4,5-tetrahydro-9(8H)-pyridazino[4,5-b][1,5]thiazepinone in 116 ml of 85% phosphoric acid 5.00 g (53.0 mmol) of phenol are added and the solution is stirred for 3 hours at 150° C. After cooling the solution is poured onto 100 g of ice-water and the pH of the mixture is adjusted to neutral with 138 g of solid sodium carbonate. The precipitate is filtered and the wet filter-cake is boiled with 12×40 ml of isopropanol. The combined isopropanol solutions are evaporated. The residue is triturated with diethyl ether, filtered and washed. In this way 6.50 g (72%) of the title compound are obtained with a melting point of 254–256° C.

EXAMPLE 31

5,7-Dimethyl-2,3,4,5-tetrahydro-6(7H)-pyridazino[4,5-b][1,5]diazepinone 0.38 g (2 mmol) of 1-benzyl-5,7-dimethyl-2,3,4,5-tetrahydro-6(7H)-pyridazino[4,5-b][1,5]diazepinone, 10 ml of abs. ethanol, 2 ml of cyclohexene and 0.20 g of Pd/C are warmed for 2 hours at 80° C. After cooling the mixture is filtered. The filtrate is evaporated and the residue is taken up in 10 ml of water, then it is shaken with 4×10 ml of ethyl acetate. The ethyl acetate phase is dried with anhydrous sodium sulphate and evaporated. The crystalline material obtained is recrystallized from 2 ml of ethyl acetate.

Yield: 0.12 g (48%), mp.: 190–192° C.

The compounds of examples 32 and 33 are prepared by the method of Example 27.

EXAMPLE 32

5-[N-Benzyl-N-(3-chloropropyl)amino]-4-chloro-2-phenyl-3(2H)-pyridazinone

Yield: 95.2%, oil.

EXAMPLE 33

5-[N-(4-Chlorobenzyl)-N-(3-chloropropyl)-amino]-4-chloro-2-methyl-3(2H)-pyridazinone Yield: 57.2%, mp.: 76–77° C.

The compounds of Examples 34 and 35 are prepared by the method of Example 20.

EXAMPLE 34

5-[N-Benzyl-N-(3-hydroxypropyl)amino]-4-chloro-2-phenyl-3(2H)-pyridazinone

Yield: 22.5%, oil.

EXAMPLE 35

5-[N-(4-Chlorobenzyl)-N-(3-hydroxypropyl)amino]-4-chloro-2-methyl-3-(2H)-pyridazinone Yield: 59.5%, oil.

What we claim is:

1. A pharmaceutical composition comprising at least one pyridazino(4,5-b)(1,5)oxazepinone, -thiazepinone or -diazepinone compound of formula (I),

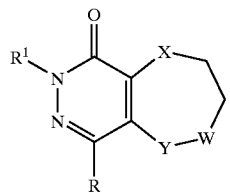

(I)

wherein

R stands for hydrogen atom or a group of formula $NHR^4$, wherein $R^4$ stands for hydrogen, $C_{1-4}$alkyl or $C_{2-5}$acyl group, $R^1$ stands for $C_{1-4}$alkyl or $C_{2-4}$alkenyl group, which may be substituted by a phenyl group, or phenyl group, W stands for methylene or carbonyl group, X and Y stand independently for oxygen or sulphur atom, SO, $SO_2$ or $NR^3$ group, wherein $R^3$ is hydrogen atom, $C_{1-4}$alkyl group or a group of formula (II),

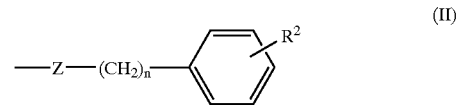

(II)

wherein $R^2$ stands for hydrogen or halogen atom, $C_{1-4}$alkoxy or nitro group or a group of formula $NHR^4$, wherein $R^4$ has the above meaning, and Z stands for methylene or carbonyl group, further n has a value of 0, 1 or 2, with the proviso that when any of X or Y stands for oxygen or sulphur atom, SO or $SO_2$ group or a group of formula $NR^3$, wherein $R^3$ stands for hydrogen atom or $C_{1-4}$alkyl group, then the other may stand only for an $NR^3$ group, wherein $R^3$ stands for a group of formula (II), wherein $R^2$, Z and n have the above meanings, or a tautomer or an acid-addition salt of all these compounds in admixture with solvents, diluents, carriers and/or additives commonly used in the pharmaceutical industry.

2. A method of treating amnesia in humans, which comprises administering to a human in need of such treatment an effective amount of a compound of claim 1.

3. A method of reducing excitotoxicity in acute or chronic neurodegeneration of excitotoxic origin, comprising the step of administering to a mammal affected by neurodegeneration of excitotoxic origin an effective amount of a compound of claim 1.

4. A method of reducing excitotoxicity in a memory disorder associated with neurodegeneration of excitotoxic origin, comprising the step of administering to a mammal affected by said memory disorder an effective amount of a compound of claim 1.

5. A method of reducing excitotoxicity in dementia of excitotoxic origin, comprising the step of administering to a mammal affected by said dementia an effective amount of a compound of claim 1.

6. A method of reducing excitotoxicity in AIDS-associated dementia of excitotoxic origin, comprising the step of administering to a mammal affected by said AIDS-associated dementia an effect amount of a compound of claim 1.

7. A method of reducing excitotoxicity in dementia induced by vascular damage of excitotoxic origin, comprising the step of administering to a mammal affected by said dementia an effective amount of a compound of claim 1.

* * * * *